United States Patent
Nielson et al.

(10) Patent No.: US 7,682,088 B2
(45) Date of Patent: Mar. 23, 2010

(54) NON-HALOGEN FIBER OPTIC CONNECTORS

(75) Inventors: Jeffrey D. Nielson, Wylie, TX (US); Matthew Cruz, Council Buffs, IA (US)

(73) Assignee: Commscope, Inc. of North Carolina, Hickory, NC (US)

( * ) Notice: Subject to any disclaimer, the term of this patent is extended or adjusted under 35 U.S.C. 154(b) by 103 days.

(21) Appl. No.: 11/765,308

(22) Filed: Jun. 19, 2007

(65) Prior Publication Data

US 2007/0292085 A1    Dec. 20, 2007

Related U.S. Application Data

(60) Provisional application No. 60/814,550, filed on Jun. 19, 2006.

(51) Int. Cl.
   G02B 6/36    (2006.01)
(52) U.S. Cl. .......................................................... 385/53
(58) Field of Classification Search .................. 385/53, 385/76–78, 86, 87, 141, 144, 145, 147
   See application file for complete search history.

(56) References Cited

U.S. PATENT DOCUMENTS

| 4,812,009 | A | | 3/1989 | Carlisle et al. |
| 4,832,615 | A | * | 5/1989 | Thakrar et al. .............. 439/272 |
| 5,076,656 | A | | 12/1991 | Briggs et al. |
| 5,181,267 | A | * | 1/1993 | Gerace et al. ................. 385/86 |
| 5,212,752 | A | * | 5/1993 | Stephenson et al. ........... 385/78 |
| 5,261,019 | A | * | 11/1993 | Beard et al. ................... 385/60 |
| 5,425,119 | A | * | 6/1995 | Lee et al. ...................... 385/86 |
| 5,461,690 | A | | 10/1995 | Lampert |
| 5,467,690 | A | * | 11/1995 | Zappala et al. ............. 99/302 P |
| 5,566,269 | A | * | 10/1996 | Eberle et al. ................ 385/137 |
| 5,915,056 | A | * | 6/1999 | Bradley et al. ................ 385/76 |
| 6,554,485 | B1 | * | 4/2003 | Beatty et al. .................. 385/72 |
| 2005/0265668 | A1 | * | 12/2005 | Martin ......................... 385/86 |
| 2007/0048475 | A1 | * | 3/2007 | Haines .................... 428/36.91 |
| 2007/0264514 | A1 | * | 11/2007 | Prigandt et al. ............. 428/494 |

* cited by examiner

*Primary Examiner*—Charlie Peng
(74) *Attorney, Agent, or Firm*—Muncy, Geissler, Olds & Lowe, PLLC

(57) ABSTRACT

A connector includes component parts, such as a strain relief boot or a grip, formed of a non-halogen polymer. The non-halogen polymer is preferably fungus resistant, lead free, and flame resistant. In a preferred embodiment, the non-halogen polymer is flexible and formed of a thermoplastic vulcanizate elastomer (TPVE), which may include rubber or polypropylenes.

11 Claims, 1 Drawing Sheet

NON-HALOGEN FIBER OPTIC CONNECTORS

This application claims the benefit of U.S. Provisional Application No. 60/814,550, filed Jun. 19, 2006, the entire contents of which are herein incorporated by reference.

BACKGROUND OF THE INVENTION

1. Field of the Invention

The present invention relates to connectors. More particularly, the present invention relates to component parts of a connector, such as a strain relief boot or a grip, which are formed of a polymer material.

2. Description of the Related Art

In certain environments, it is very important to control the gases released by burning materials. For example, in confined environments like vehicles (e.g. airplanes, trains, ships or submarines), the environment and air quality must be preserved as best as possible in the event of a fire.

Heretofore, fiber optic cables have included flexible plastic parts on their connectors, such as a strain relief boot, and less flexible plastic parts, such as a grip. U.S. Pat. Nos. 4,812,009, 5,461,690, and 5,915,056 illustrate a fiber optic connector with a strain relief boot and grip, each of these patents is incorporated herein by reference. In certain environments (e.g. damp areas on ships), polymer parts of a connector are usually constructed to include a fungus resisting additive, such as a biocide.

SUMMARY OF THE INVENTION

The Applicants have appreciated drawbacks in the connectors of the background art.

The plastic or flexible parts (e.g. strain relief boot, grip) of the connectors of the background art include several materials including at least one of lead or elements from the halogen group. For example, the strain relief boots of the background art were made of TPE (thermal plastic elastomer), PVC, fluoroelastomer, etc. One known trademarked material used for such boots, produced by DUPONT, is known as VITON.

Burning these types of materials produces such gases as chlorine, bromine and/or fluorine. Such gases are harmful to the health of personnel in the area and can also be corrosive and damaging to other equipment in the area, which can lead to additional damage by a fire. Further, the additives in such materials of the background art to resist fungus also can produce harmful and/or corrosive gases when burned.

Therefore, Applicants have appreciated a need in the art for a non-halogen, fungus resistant, lead free, flame resistant, polymer that could be formed into a plastic component of a connector, such as a flexible strain relief boot or a grip of a connector, such as a fiber optic connector.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limits of the present invention, and wherein.

DETAILED DESCRIPTION OF EMBODIMENTS OF THE INVENTION

Figure 1:
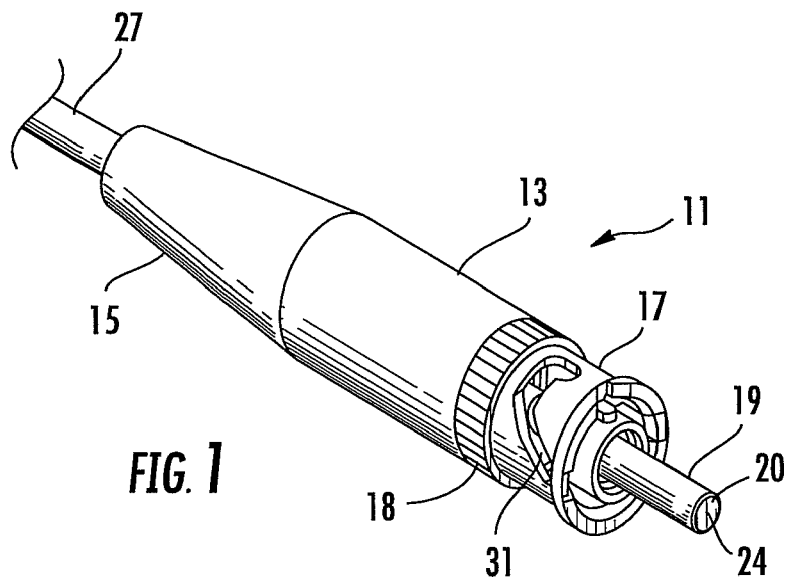
FIG. 1 is a perspective of a fiber optic connector in accordance with the present invention.

The present invention is now described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper", "lateral", "left", "right" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. The device may be otherwise oriented (rotated 90 degrees or at other orientations) and the descriptors of relative spatial relationships used herein interpreted accordingly.

FIG. 1 is an illustration of a fiber optic connector 11 in accordance with the present invention. Although an ST® type fiber optic connector 11 is shown, other types of fiber optic connectors could include the inventive polymer component parts (e.g. boot, grip) of the present invention, such as the SC, LC, MT, MU, FC, 29504, 38999, and ROC type fiber optic connectors. Also, other types of connectors besides fiber optic connectors could include the inventive polymer component parts, such as coaxial connectors, twisted pair connectors, patch cord connectors, and speaker wire connectors.

Figure 2:
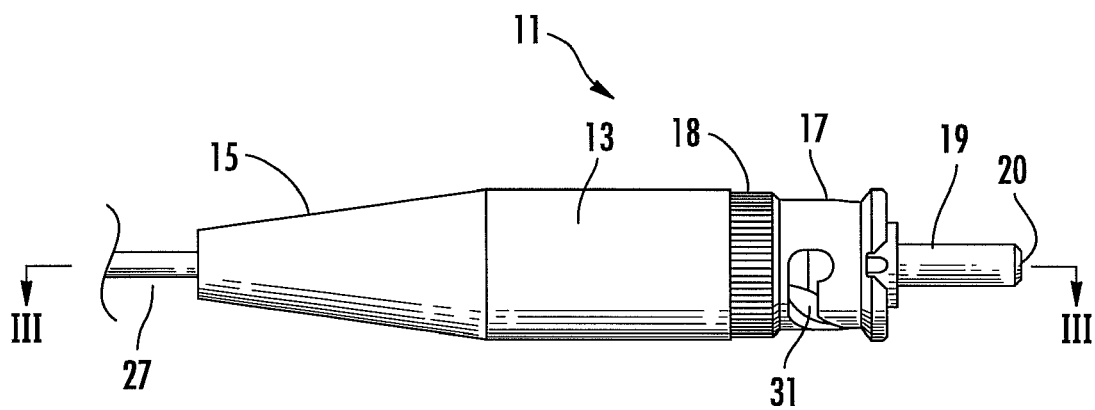
FIG. 2 is a side view of the fiber optic connector of FIG. 1.
Figure 3:
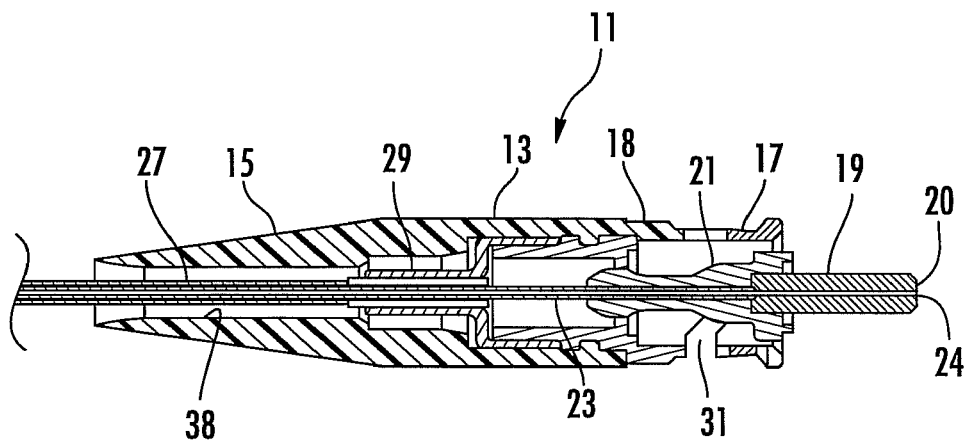
FIG. 3 is a cross sectional view taken along line III-III of FIG. 2.

As illustrated in FIGS. 1-3, the fiber optic connector 11 includes a grip 13 and a strain relief boot 15 formed of an inventive non-halogen polymer in accordance with the present invention, as will be described in more detail hereinafter. The fiber optic connector 11 includes a coupling nut 17. The coupling nut 17 is typically formed of metal and may include one or more knurled sections 18 to facilitate rotation of the coupling nut 17 by a user.

A ferrule 19 extends from a jack-mating end of the connector 11. The Ferrule 19 is typically formed of ceramic and presents a polished end 20 with an opening to expose an end of an optic fiber 24. The ferrule 19 is held by a holder 21.

The grip 13 and the strain relief boot 15 have a central bore 38. A fiber optic cable 27 passes through the central bore 38 toward the jack-mating end of the connector 11. Inside the connector 11, a jacket and strength members, are stripped from the fiber optic cable 27 to reveal a coated fiber 23. The coated fiber 23 is held in place by a crimp sleeve 29.

After passing through the holder 21, the coating on the coated fiber 23 is optionally removed before the optic fiber 24 passes through a central bore in the ferrule 19. The optic fiber 24 may be held in the ferrule with an epoxy. The end of the optic fiber 24 is polished along with the end 20 of the ferrule 19.

A bayonet-type locking feature of the fiber optic connector 11 is accomplished by slot 31. The slot 31 is formed in the coupling nut 17. A mating jack (not shown) would include a pin (not shown) to ride in the slot 31 and lock the fiber optic connector 11 to the jack.

In accordance with the present invention, the grip 13 and strain relief boot 15 are formed of a non-halogen polymer, like a thermoplastic polymer, such as a thermoplastic vulcanite polymer. More specifically, the grip 13 and the strain relief boot 15 of the present invention may be made of a flexible thermoplastic vulcanizate elastomer (TPVE). Such materials do not emit chlorine, bromine or fluorine when burned and inherently inhibit fungal growth without the need to add biocides.

A review of the patent literature will reveal that such thermoplastic vulcanizates are known compositions, and can include rubber and polypropylenes. Such compositions are used in diverse manufacturing arts, however, to the best of the Applicants' knowledge such materials have not been used in the communication connector art and particularly have not been used to construct connector parts, such as a strain relief boot or a grip of a fiber optic cable connector. Applicants have appreciated drawbacks in the background art connectors, and looked to non-analogous arts to find a material which could remedy the drawbacks in order to produce a superior performing communications connector, which is particularly well-suited for an emergency fire condition in a confined environment.

Applicants appreciate that a trace amount of lead may be present in a lead-free material, and that a trace amount of halogen may be present in a non-halogen material. The terms are meant to encompass materials with such trace amounts whether occurring naturally or by result of man or machine.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

We claim:

1. An apparatus comprising: a fiber optic communications connector having a component part formed of a non-halogen polymer, wherein said non-halogen polymer is a thermoplastic vulcanizate elastomer (TPVE) including both rubber and polypropylene.

2. The apparatus of claim 1, wherein said component part is a strain relief boot.

3. The apparatus of claim 1, wherein said component part is a grip.

4. The apparatus of claim 1, wherein said non-halogen polymer is lead free.

5. The apparatus of claim 4, wherein said component part is a strain relief boot.

6. The apparatus of claim 4, wherein said component part is a grip.

7. A fiber optic connector comprising:
a strain relief boot formed of a non-halogen, flexible polymer, wherein said non-halogen, flexible polymer is a thermoplastic vulcanizate elastomer (TPVE) including both rubber and polypropylene.

8. The fiber optic connector of claim 7, wherein said polymer is lead free.

9. A fiber optic connector comprising:
a strain relief boot formed of materials which do not emit chlorine, bromine or fluorine when burned, and wherein said materials constitute a thermoplastic vulcanizate elastomer (TPVE) including both rubber and polypropylene.

10. The fiber optic connector of claim 9, wherein said materials used to form said strain relief boot inhibit fungal growth without possessing biocide additives.

11. The connector of claim 9, wherein said materials are lead free.

* * * * *